(12) United States Patent
Walters et al.

(10) Patent No.: US 12,083,196 B2
(45) Date of Patent: Sep. 10, 2024

(54) PERSONAL CLEANSING COMPOSITIONS WITH SURFACTANTS FOR INCREASED FOAM PERFORMANCE

(71) Applicant: ECOLAB USA INC., Saint Paul, MN (US)

(72) Inventors: Kerrie E. Walters, Saint Paul, MN (US); Erik C. Olson, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 180 days.

(21) Appl. No.: 17/451,893

(22) Filed: Oct. 22, 2021

(65) Prior Publication Data

US 2022/0142879 A1 May 12, 2022

Related U.S. Application Data

(60) Provisional application No. 63/198,738, filed on Nov. 9, 2020.

(51) Int. Cl.
| | | |
|---|---|---|
| *A61K 8/00* | (2006.01) | |
| *A61K 8/04* | (2006.01) | |
| *A61K 8/37* | (2006.01) | |
| *A61K 8/44* | (2006.01) | |
| *A61K 8/46* | (2006.01) | |
| *A61K 8/60* | (2006.01) | |

(Continued)

(52) U.S. Cl.
CPC ............... *A61K 8/046* (2013.01); *A61K 8/37* (2013.01); *A61K 8/447* (2013.01); *A61K 8/463* (2013.01); *A61K 8/466* (2013.01); *A61K 8/602* (2013.01); *A61Q 5/02* (2013.01); *A61Q 19/10* (2013.01)

(58) Field of Classification Search
CPC ....................................................... A61K 8/466
See application file for complete search history.

(56) References Cited

U.S. PATENT DOCUMENTS 3,941,722 A 3/1976 Shevlin
5,254,334 A 10/1993 Ramirez et al.
(Continued)

FOREIGN PATENT DOCUMENTS

BR 112012033245 A2 8/2016
CN 103349620 A 10/2013
(Continued)

OTHER PUBLICATIONS

International Searching Authority in connection with PCT/US2021/058419 filed Nov. 8, 2021, "The International Search Report and the Written Opinion of the International Searching Authority, or the Declaration", 24 pages, mailed Mar. 2, 2022.

*Primary Examiner* — Necholus Ogden, Jr.
(74) *Attorney, Agent, or Firm* — McKee, Voorhees & Sease, PLC

(57) ABSTRACT

Personal cleansing compositions are disclosed with a synergistic combination of anionic surfactants in that impart early formation of foam with lasting foam stability. An anionic sulfate surfactant is provided in combination with a bio renewable alkyl sulfoacetate/alkyl ethoxy sulfoacetate surfactant for use as a liquid hand soap, liquid body wash, antimicrobial or sanitizing composition, or shampoo. The surfactant combination is also less irritating to skin. Methods of use and methods of making such compositions are also disclosed.

17 Claims, 5 Drawing Sheets

(51) Int. Cl.
*A61Q 5/02* (2006.01)
*A61Q 19/10* (2006.01)

(56) References Cited

U.S. PATENT DOCUMENTS

| | | | |
|---|---|---|---|
| 5,409,706 | A | 4/1995 | Ramirez et al. |
| 5,637,758 | A | 6/1997 | Sajic et al. |
| 5,665,332 | A | 9/1997 | Mundschenk et al. |
| 6,086,856 | A | 7/2000 | Saferstein et al. |
| 6,337,066 | B1 | 1/2002 | Jacquier |
| 6,723,330 | B2 | 4/2004 | Bergquist |
| 7,482,314 | B2 | 1/2009 | Grimes et al. |
| 8,053,400 | B2 | 11/2011 | Dong et al. |
| 8,329,626 | B2 | 12/2012 | Gunn et al. |
| 8,329,627 | B2 | 12/2012 | Gunn et al. |
| 8,343,902 | B2 | 1/2013 | Walters et al. |
| 9,539,185 | B2 | 1/2017 | Sato et al. |
| 9,636,284 | B2 | 5/2017 | Vierling et al. |
| 9,901,524 | B2 | 2/2018 | Aubrun et al. |
| 2003/0064042 | A1 | 4/2003 | Bergquist et al. |
| 2004/0197270 | A1 | 10/2004 | Mundschenk |
| 2004/0234484 | A1 | 11/2004 | Peffly et al. |
| 2005/0058672 | A1 | 3/2005 | Gupta |
| 2005/0124515 | A1 | 6/2005 | Ospinal et al. |
| 2005/0153853 | A1 | 7/2005 | Sajic et al. |
| 2007/0004611 | A1 | 1/2007 | Ospinal et al. |
| 2007/0237834 | A1 | 10/2007 | Gupta |
| 2008/0058236 | A1 | 3/2008 | Ospinal et al. |
| 2011/0319307 | A1 | 12/2011 | Gunn et al. |
| 2013/0034515 | A1 | 2/2013 | Stone et al. |
| 2014/0094395 | A1 | 4/2014 | Berbel et al. |
| 2015/0157548 | A1 | 6/2015 | De Feij et al. |
| 2016/0235639 | A1 | 8/2016 | Mathonneau et al. |
| 2016/0235643 | A1 | 8/2016 | Mathonneau et al. |
| 2019/0282481 | A1 | 9/2019 | Thomas et al. |
| 2019/0365622 | A1 | 12/2019 | Botto et al. |
| 2022/0257487 | A1* | 8/2022 | Laurent .................. A61Q 19/10 |
| 2023/0062740 | A1* | 3/2023 | Chang .................... A61K 8/731 |

FOREIGN PATENT DOCUMENTS

| | | | |
|---|---|---|---|
| CN | 106265364 A | 1/2017 | |
| CN | 106924064 A | 7/2017 | |
| CN | 107496183 A | 12/2017 | |
| FR | 2829021 A1 | 3/2003 | |
| FR | 3013966 A1 | 6/2015 | |
| FR | 3013968 A1 | 6/2015 | |
| JP | S62240390 A | 10/1987 | |
| JP | 2017081880 A | 5/2017 | |
| KR | 1585635 B1 | 1/2016 | |
| WO | WO-0123517 A1 * | 4/2001 | ............. A61K 8/442 |
| WO | 2001085104 A1 | 11/2001 | |
| WO | 2015079026 A1 | 6/2015 | |
| WO | 2015158637 A1 | 10/2015 | |

\* cited by examiner

PERSONAL CLEANSING COMPOSITIONS WITH SURFACTANTS FOR INCREASED FOAM PERFORMANCE

CROSS-REFERENCE TO RELATED APPLICATION

This application claims priority under 35 U.S.C. § 119 to Provisional Application U.S. Ser. No. 63/198,738, filed on Nov. 9, 2020, which is herein incorporated by reference in its entirety including without limitation, the specification, claims, and abstract, as well as any figures, tables, or examples thereof.

FIELD

A liquid personal care composition with persistent and early foam generation with bio renewable surfactants and decreased skin irritation and improved skin feel.

BACKGROUND

Consumer preferences in personal care compositions have long required high foaming performance. These compositions require synergies between different surfactants to boost foaming performance, however many foaming surfactants, which are typically anionic, are not bio renewable and often are irritating to the skin. Thus, new formulations of hand soaps, bodywashes and the like, must satisfy not only foam requirements but also epidermal mildness. Increasing regulations and biorenewablility are also important factors that must be considered. Achieving a combination of surfactants that satisfy all of these competing objectives can be difficult and unpredictable. Many foaming surfactants can negatively impact antimicrobial activity. Further many of the surfactants normally used in personal care applications have high cleansing abilities and foaming characteristics but are also potentially harsh on skin and hair and are not bio renewable.

SUMMARY

Personal cleansing compositions are disclosed with a synergistic combination of anionic surfactants in that impart early formation of foam with lasting foam stability. The combination of surfactants also does not negatively impact detergency or antimicrobial activity of the composition and improve skin feel with bio renewable surfactant sources. According the disclosure the anionic surfactant combination includes anionic surfactants including their salts forms, of a sulfate surfactant or a sulfonated alcohol and a naturally based bio renewable alkyl sulfoacetate/alkyl ethoxy sulfoacetate surfactant. In certain embodiments the composition is free of sulfonated fatty acids or free of additional anionic surfactants.

According to the disclosure, the surfactants are employed to enhance foaming performance of personal care body wash, hair wash, hand wash, and antimicrobial compositions, such as hand sanitizers, and employ the combination of surfactants in addition to other personal care components such as preservatives, humectants, thickeners, skin conditioners, additional nonionic, cationic, and/or zwitteronic surfactants and/or a carrier.

In preferred embodiments the anionic sulfate surfactant is an alkyl sulfate, alkyl ethoxysulfate, and/or a sulfate of alkylpolysaccharide such as the sulfate of alkylpolyglucoside, including their salt forms. The bio renewable alkyl sulfoacetate/alkyl ethoxy sulfoacetate surfactant is preferably lauryl sulfoacetate, and a carrier.

In a further embodiment, there is provided a composition suitable for use as a liquid hand soap, liquid body wash, antimicrobial or sanitizing composition, or shampoo, including: lauryl sulfoacetate, and laureth sulfate, additional additives, and water. It will be understood that while specific ingredients may be utilized in any amount within the specified ranges, that the relative amounts of ingredients and/or optional additives or thickeners selected shall add to 100% of a finished composition.

In some embodiments, the invention relates to a non-aerosol antimicrobial composition with a lauryl sulfoacetate, and laureth sulfate, a preservative/antimicrobial, and water. In some embodiments, the invention relates to a non-aerosol antimicrobial composition with a sodium lauryl sulfoacetate, laureth sulfate at least one additional surfactant, a preservative/antimicrobial, and water.

Further embodiments of the present invention may additionally incorporate emollients, skin conditioners, viscosity adjusters, rheological modifiers, fragrances, colorants, opacifiers, pearlescent agents, herbal extract, vitamins, terpenoids, chelating agents, preservatives, and the like. Additional embodiments may also be configured to be suitable as soap powder, shower gel, bath soap or bath beads, denture cleanser or other personal care compositions where high stable foaming is desired.

DETAILED DESCRIPTION

Figure 1:
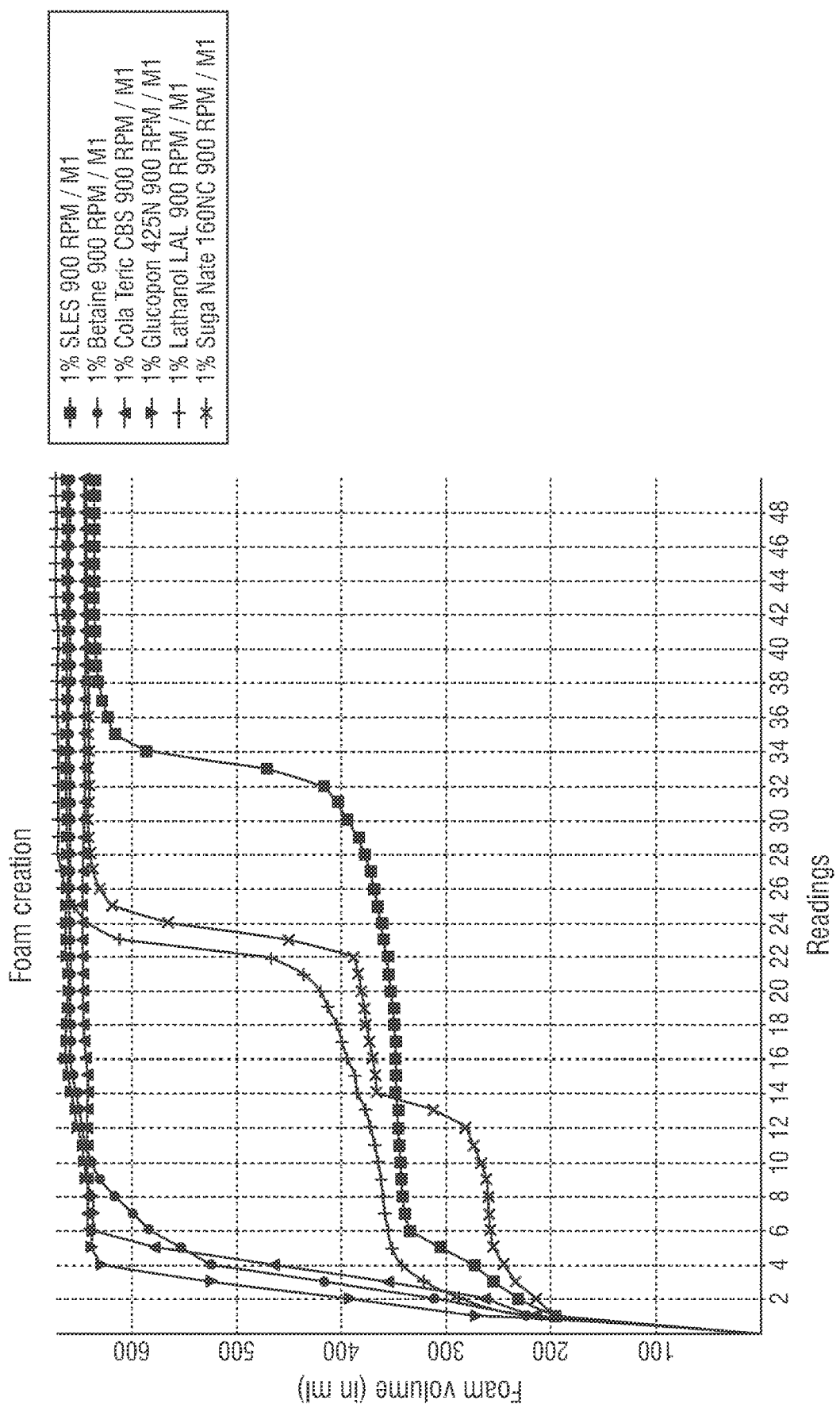
FIG. 1 is a graphical representation of the foam creation for 1 wt. % surfactant solutions, including SLES, betaine, Cola® Teric CBS, Glucopon® 425N, Lathanol® LAL, and Suga® Nate 160NC.

While the presently described technology will be described in connection with one or more preferred embodiments, it will be understood by those skilled in the art that the technology is not limited to only those particular embodiments. To the contrary, the presently described technology includes all alternatives, modifications, and equivalents as may be included within the spirit and scope of the appended claims.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

The term "actives" or "percent actives" or "percent by weight actives" or "actives concentration" are used interchangeably herein and refers to the concentration of those ingredients involved in cleansing expressed as a percentage minus inert ingredients such as water or salts.

As used herein, "weight percent," "wt. %," "percent by weight," "% by weight," and variations thereof refer to the concentration of a substance as the weight of that substance divided by the total weight of the composition and multiplied by 100. It is understood that, as used here, "percent," "%," and the like are intended to be synonymous with "weight percent," "wt. %," etc.

The term "about," as used herein, modifying the quantity of an ingredient in the compositions of the invention or employed in the methods of the invention refers to variation in the numerical quantity that can occur, for example, through typical measuring and liquid handling procedures used for making concentrates or use solutions; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about," the claims include equivalents to the quantities. All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The term "alkyl" or "alkyl groups," as used herein, refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups. In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed bacteriocidal and the later, bacteriostatic. A sanitizer and a disinfectant are, by definition, agents which provide antibacterial or bacteriocidal activity. In contrast, a preservative is generally described as an inhibitor or bacteriostatic composition.

The term "sanitizer," as used herein, refers to an agent that reduces the number of bacterial contaminants to safe levels as judged by public health requirements. The recitation of numerical ranges by endpoints includes all numbers subsumed within that range (e.g., 1 to 5 includes 1, 1.5, 2, 2.75, 3, 3.80, 4, and 5).

The terms "include" and "including" when used in reference to a list of materials refer to but are not limited to the materials so listed.

Personal Cleansing Compositions

The cleansing compositions of disclosure include a bio renewable alkyl sulfoacetate surfactant in combination with a sulfate anionic surfactant or sulfonated alcohol for early and stable foam generation in nonaerosol cleansing compositions. According to the disclosure, the surfactant combination may be used to enhance foaming performance of personal care body wash, hair wash, hand wash, and antimicrobial compositions, such as hand sanitizers. In certain embodiments the combination of surfactants may be used in formulations with additional personal care components such as preservatives, humectants, thickeners, skin conditioners, additional nonionic, cationic, and/or zwitteronic surfactants and carriers.

Sample Formulations of the personal cleansing compositions are shown in the Table below with additional personal care components.

Sample Concentrate Cleansing Formulations

| Component | Ranges | Preferred Ranges | More Preferred Ranges |
| --- | --- | --- | --- |
| Carrier | 1-50% | 5-40% | 10-30% |
| Anionic sulfate surfactant | 1-45% | 5-40% | 10-35% |
| Additional nonionic, cationic, or zwitteronic surfactant | 0.1-20% | 0.5-15% | 1-10% |
| Humectant | 0.1-20% | 0.5-15% | 1-10% |
| Thickener | 0.001-2% | 0.005-1% | 0.01-0.5% |

-continued

| Component | Ranges | Preferred Ranges | More Preferred Ranges |
| --- | --- | --- | --- |
| Skin Conditioner | 0.01-15% | 0.05-10% | 0.1-5% |
| Alkyl sulfoactetate | 0.01-10% | 0.05-7.5% | 0.1-5% |
| Preservative | 0.01-10% | 0.05-7.5% | 0.1-5% |

Sample Use Cleansing Formulations

| Component | Ranges | Preferred Ranges | More Preferred Ranges |
| --- | --- | --- | --- |
| Carrier | 40-90% | 45-85% | 50-90% |
| Anionic sulfate surfactant | 0.5-20% | 1-15% | 5-10% |
| Additional nonionic, cationic, or zwitteronic surfactant | 0.1-20% | 0.5-15% | 1-10% |
| Humectant | 0.1-20% | 0.5-15% | 1-10% |
| Thickener | 0.001-2% | 0.005-1% | 0.01-0.5% |
| Skin Conditioner | 0.01-15% | 0.05-10% | 0.1-5% |
| Alkyl sulfoactetate | 0.01-10% | 0.05-7.5% | 0.1-5% |
| Preservative | 0.01-10% | 0.05-7.5% | 0.1-5% |

Alkyl Sulfoacetate/Ethoxylated Alkyl Sulfoacetate

The alkyl sulfoacetate or ethoxylated alkyl sulfoacetate preferably has the general chemical structure:

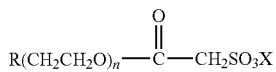

$$R(CH_2CH_2O)_n-\overset{O}{\underset{\|}{C}}-CH_2SO_3X$$

wherein R is a fully saturated or unsaturated C5-C21 hydrocarbyl group, n is an integer between 0 and 6, and X is hydrogen, an alkaline metal, ammonium, organic amine, or alkaline earth metal. Preferred alkyl sulfoacetate compounds include, without limitation, sodium lauryl sulfoacetate, and/or ethoxylated sodium lauryl sulfoacetate.

It should be understood by those skilled in the art that suitable alkyl sulfoacetates for purposes of the presently described technology may be produced by sulfitating an alkyl alcohol mono-chloroacetate with a sulfitating agent such as sodium sulfite and sodium metabisulfite, or may be commercially obtained from Stepan Company, Northfield Ill., as LATHANOL® LAL (sodium lauryl sulfoacetate).

Sodium Lauryl Sulfoacetate is bio renewable and is derived from coconut and palm oils; a safe, skin-friendly surfactant (foaming agent) for both skin and hair. This mild plant-derived surfactant creates a rich, luxurious lather that effectively removes surface oil, dirt, and bacteria without stripping or drying sensitive skin or hair. It cannot penetrate the skin and is non-irritating. It also will dissolve more readily in water, thus providing superior rinse-ability.

Anionic Sulfate Surfactant

Anionic sulfate surfactants suitable for use in the present compositions include the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl)glucamine sulfates, and sulfates of alkyl polysaccharides such as the sulfates of alkylpolyglucoside. In some embodiments the composition is free of sulfonated surfactants or is free of any additional anionic surfactants.

In a preferred embodiment at least one of the anionic sulfate surfactants is laureth sulfate, more preferably a sodium laureth sulfate, or SLES. Sodium laureth sulfates are synthetic cleansing agent that are small molecule ingredients which can penetrate the skin and can cause minor skin irritation, Additional Anionic Surfactant In embodiments with additional anionic surfactants, in general these are all surface active substances which are categorized as anionics because the charge on the hydrophobe is negative; or surfactants in which the hydrophobic section of the molecule carries no charge unless the pH is elevated to neutrality or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium, and potassium impart water solubility; ammonium and substituted ammonium ions provide both water and oil solubility; and calcium, barium, and magnesium promote oil solubility.

As those skilled in the art understand, anionics are excellent detersive surfactants and are therefore traditionally favored additions to heavy duty detergent compositions. Generally, anionics have high foam profiles which are useful for the present foaming cleansing compositions. Anionic surface-active compounds are useful to impart special chemical or physical properties other than detergency within the composition.

The majority of large volume commercial anionic surfactants can be subdivided into five major chemical classes and additional sub-groups known to those of skill in the art and described in "Surfactant Encyclopedia," Cosmetics & Toiletries, Vol. 104 (2) 71-86 (1989).

The first class includes acylamino acids (and salts), such as acylgluamates, acyl peptides, sarcosinates (e.g. N-acyl sarcosinates), taurates (e.g. N-acyl taurates and fatty acid amides of methyl tauride), and the like. The second class includes carboxylic acids (and salts), such as alkanoic acids (and alkanoates), ester carboxylic acids (e.g. alkyl succinates), ether carboxylic acids, and the like. The third class includes sulfonic acids (and salts), such as isethionates (e.g. acyl isethionates), alkylaryl sulfonates, alkyl sulfonates, sulfosuccinates (e.g. monoesters and diesters of sulfosuccinate), and the like. A particularly preferred anionic surfactant is alpha olefin sulfonate. The fourth class includes sulfonic acids (and salts), such as isethionates (e.g. acyl isethionates), alkylaryl sulfonates, alkyl sulfonates, sulfosuccinates (e.g. monoesters and diesters of sulfosuccinate), and the like. The fifth class includes sulfuric acid esters (and salts), such as alkyl ether sulfates, alkyl sulfates, and the like. The fifth class includes sulfuric acid esters (and salts), such as alkyl ether sulfates, alkyl sulfates, and the like. A particularly preferred anionic surfactant is sodium laurel ether sulfate.

Anionic sulfate surfactants suitable for use in the present compositions include the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl)glucamine sulfates, and sulfates of alkylpolysaccharides such as the sulfates of alkylpolyglucoside (the nonionic nonsulfated compounds being described herein). Ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from 5 to 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives.

Examples of suitable synthetic, water soluble anionic detergent compounds include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from 5 to 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives.

Anionic carboxylate surfactants suitable for use in the present compositions include the alkyl ethoxy carboxylates, the alkyl polyethoxy polycarboxylate surfactants and the soaps (e.g. alkyl carboxyls). Secondary soap surfactants (e.g. alkyl carboxyl surfactants) useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary soap surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present.

Other anionic detergents suitable for use in the present compositions include olefin sulfonates, such as long chain alkene sulfonates, long chain hydroxyalkane sulfonates or mixtures of alkenesulfonates and hydroxyalkane-sulfonates. Also included are the alkyl sulfates, alkyl poly(ethyleneoxy) ether sulfates and aromatic poly(ethyleneoxy)sulfates such as the sulfates or condensation products of ethylene oxide and nonyl phenol (usually having 1 to 6 oxyethylene groups per molecule). Resin acids and hydrogenated resin acids are also suitable, such as rosin, hydrogenated rosin, and resin acids and hydrogenated resin acids present in or derived from tallow oil.

The particular salts will be suitably selected depending upon the particular formulation and the needs therein.

Further examples of suitable anionic surfactants are given in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23.

Additional anionic surfactants, if present, may be included in the composition in any detersive amount which can range typically from about 0 wt. % to about 10 wt. % of the cleansing composition. In a preferred embodiment, about 0 wt. % to about 15 wt. % and more preferably from about 0 wt. % to about 20 wt. %.

Additional Other Surfactants

The compositions can comprise one or more additional surfactants. Preferred additional surfactants include foaming amphoteric, nonionic, and cationic surfactants.

The compositions of the invention can comprise the additional other surfactants in a concentration of between about 0.1 wt. % and about 20 wt. %, preferably about 0.5 wt. % and about 15 wt. %, and more preferably between about 1 wt. % and about 10 wt. %.

Cationic Surfactants

Examples of cationic surfactants suitable as foaming agents include, but are not limited to, quaternized polysaccharides, alkyl polysaccharides, alkoxylated amines, alkoxylated ether amines, and mixtures thereof.

Cationic surfactants preferably include, more preferably refer to, compounds containing at least one long carbon chain hydrophobic group and at least one positively charged nitrogen. The long carbon chain group may be attached directly to the nitrogen atom by simple substitution; or more preferably indirectly by a bridging functional group or groups in so-called interrupted alkylamines and amido amines. Such functional groups can make the molecule more hydrophilic and/or more water dispersible, more easily water solubilized by co-surfactant mixtures, and/or water soluble. For increased water solubility, additional primary, secondary or tertiary amino groups can be introduced, or the amino nitrogen can be quaternized with low molecular weight alkyl groups. Further, the nitrogen can be a part of branched or straight chain moiety of varying degrees of unsaturation or of a saturated or unsaturated heterocyclic ring. In addition, cationic surfactants may contain complex linkages having more than one cationic nitrogen atom.

The surfactant compounds classified as amphoterics and zwitterions are themselves typically cationic in near neutral to acidic pH solutions and can overlap surfactant classifications. Polyoxyethylated cationic surfactants generally behave like nonionic surfactants in alkaline solution and like cationic surfactants in acidic solution. At pH levels less than 4, amine oxide type surfactants can also have some cationic character.

The simplest cationic amines, amine salts and quaternary ammonium compounds can be schematically drawn thus:

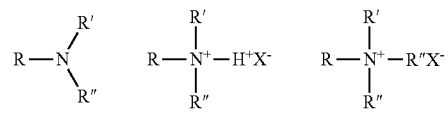

in which, R represents a long alkyl chain, R', R", and R'" may be either long alkyl chains or smaller alkyl or aryl groups or hydrogen and X represents an anion. The amine salts and quaternary ammonium compounds are preferred for practical use in this invention due to their high degree of water solubility.

The majority of large volume commercial cationic surfactants can be subdivided into four major classes and additional sub-groups known to those or skill in the art and described in "Surfactant Encyclopedia", Cosmetics & Toiletries, Vol. 104 (2) 86-96 (1989). The first class includes alkylamines and their salts. The second class includes alkyl imidazolines. The third class includes ethoxylated amines. The fourth class includes quaternaries, such as alkylbenzyldimethylammonium salts, alkyl benzene salts, heterocyclic ammonium salts, tetra alkylammonium salts, and the like. Cationic surfactants are known to have a variety of properties that can be beneficial in the present compositions. These desirable properties can include detergency in compositions of or below neutral pH, antimicrobial efficacy, thickening or gelling in cooperation with other agents, and the like.

Examples of cationic surfactants includes the chloride, bromide, or methosulfate salts of alkyltrimethylammonium species where the alkyl group chain length is C8-C18, the preferred alkyl chain length is C8-16, and the most preferred alkyl chain length is C8-C14.

Nonionic Surfactants

Examples of nonionic surfactants suitable as foaming agents include, but are not limited to, alcohol ethoxylates, fatty acid ethoxylates, alkyl phenol ethoxylate, mono-alkonaolamide ethoxylates, sorbitan esters and their ethoxylated derivatives, ethoxylated fats and oils, amine ethoxylates, ethylene oxide-propylene oxide co-polymers, glycol esters, glycerol and polyglycerol esters, sucrose esters mono and polysaccharides surfactants, such as alkyl polyglucosides.alkyl alcohol ethoxylates, capped alkyl alcohol ethoxylates, fatty alcohol ethoxylate propoxylates, ethoxylated siloxane copolymers (PEG dimethicone) including alkyl capped, PEG/PPG dimethicones, mixtures thereof, or the like. Preferred substituted amides include, but are not limited to, glucosamides.

The antimicrobial composition can contain a nonionic surfactant component that includes a detersive amount of nonionic surfactant or a mixture of nonionic surfactants. Typically, a nonionic surfactant has a hydrophobic region, such as a long chain alkyl group or an alkylated aryl group, and a hydrophilic group comprising an ethoxy and/or other hydrophilic moieties.

Phospholipids and Phospholipid Derivatives

Phospholipid and/or phospholipid derivative surfactants can also be included. Preferred phospholipid derivatives include, but are not limited to, diester and triester phosphatides with multiple chain groups, and mixtures thereof. Preferred phospholipid surfactants include but are not limited to coco PG-dimonium chloride phosphate, myristamidopropyl PG-dimonium chloride phosphate, linoleamidopropyl PG-dimonium chloride phosphate, stearamidopropyl PG-dimonium chloride phosphate, and mixtures thereof Amphoteric Surfactants Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" Cosmetics & Toiletries, Vol. 104 (2) 69-71 (1989), which is herein incorporated by reference in its entirety. The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof; and an aliphatic substituent of from about 8 to 18 (e.g., 12) carbon atoms. Such a surfactant can also be considered an alkyl amphodicarboxylic acid. These amphoteric surfactants can include chemical structures represented as: C12-alkyl-C(O)—NH—CH2-CH2-N+(CH2-CH2-CO2Na)2-CH2-CH2-OH or C12-alkyl-C(O)—N(H)—CH2-CH2-N+(CH2-CO2-Na)2-CH·2-CH2-OH.

Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate.

Examples of zwitterionic surfactants having the structures listed above include: 4-[N,N-di(2-hydroxyethyl)-N-octadecylammonio]-butane-1-carboxylate; 5-[S-3-hydroxypropyl-S-hexadecylsulfonio]-3-hydroxypentane-1-sulfate; 3-[P,P-diethyl-P-3,6,9-trioxatetracosanephosphonio]-2-hydroxypropane-1-ph-osphate; 3[N,N-dipropyl-N-3-dodecoxy-2-hydroxypropyl-ammonio]-propane-1-ph-osphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxyl-ate; 3-[S-ethyl-S-(3-dodecoxy-2-hydroxypropyl)sulfonio]-propane-1-phosphat-e; 3[P,P-dimethyl-P-dodecylphosphoniol-propane-1-phosphonate;

and S]N,N-di(3-hydroxypropyl)-N-hexadecylammoniol-2-hydroxy-pentane-1-sulfate-. The alkyl groups contained in said detergent surfactants can be straight or branched and saturated or unsaturated.

For example, the compositions can include cocoamido propyl betaine, however, the level of betaine in the system can have a negative impact on efficacy requiring additional active ingredient to compensate for efficacy. Due to this interaction, the amount of betaine in the system is preferably less than 1%, more preferably less than 0.5%, and most preferably free of betaine.

Preferred secondary foaming agents include, lauryl trimethyl ammonium chloride, palmitamidopropyl trimonium chloride, diester phosphatides with multiple chain groups, triester phosphatides, coco PG-dimonium chloride phosphate, myristamidopropyl PG-dimonium chloride phosphate, linoleamidopropyl PG-dimonium chloride phosphate, stearamidopropyl PG-dimonium chloride phosphate, and mixtures thereof.

Preferably, the compositions comprise from about 0.1 wt-% to about 5 wt-% of additional surfactant, more preferably from about 0.5 wt-% to about 4.5 wt additional surfactant, and most preferably from about 1.5 wt-% to about 4 wt-% additional surfactant.

Humectants

Humectants and emollients are useful skin conditioning agents that moisturize and protect the skin and provide a lasting, soft conditioned after feel. The present composition may include one or more such components. Commonly, humectants include, but are not limited to, aliphatic alcohols, polyhydroxy alcohols, glycols, polyols, sorbitol, and ureas. Useful emollients include, but are not limited to, silicone polymers, phospholipid complexes, esters, fatty acids, alcohols, glycols, and polyols. Other humectants and emollients useful in the compositions are known in the art. Preferably, the compositions may include hexylene glycol, glycerin, and/or sorbitol.

Other useful skin feel components and conditioners include, but are not limited to, water soluble silicone polymers, such as dimethicones, cationic polymers, and nonionic polymers, such as certain cellulosic materials. Particularly useful components include polyquaternium-7, cetyl hydroxyethylcellulose, PEG-8 dimethicone. In some embodiments, the compositions may include a water-soluble silicone polymer such as PEG-8 dimethicone.

The humectant or combination thereof in total is present in the composition in an amount from about 0.1 wt. % to about 40 wt. %, preferably from about 0.5 wt. to about 35 wt. %, and more preferably from about 1 wt. % to about 30 wt. %.

Skin Conditioner

The composition can include at least one skin conditioner to provide skin moisturizing, skin softening, skin barrier maintenance, anti-irritation, or other skin health benefits. Some non-limiting examples of additional skin conditioners include alkyl benzoate, myristyl myristate, cetyl myristate, gelatin, carboxylic acid, lsactoc acid, glyceryl dioleate, methyl laurate, PPG-9 laurate, lauryl lacylate allantoin, octyl palmitate, lanolin, propylene glycol, butylene glycol, ethylene glycol, glycerol caprylate, caprylyl glycol, monobutyl ether, glycerine, fatty acids, proline, natural oils such as almond, mineral, canola, sesame, soybean, pyrrolidine, wheat germ, hydrolyzed wheat protein, hydrolyzed oat protein, hydrolyzed collagen, corn, peanut and olive oil, isopropyl myristate, myristyl alcohol, aloe vera, algae extract, gluconic acid, hydrolyzed silk protein, 1,3-propane-diol, Vitamin E, nicatinamide, stearyl alcohol, isopropyl palmitate, sorbitol, amino acid complexes, panthenol, allantoin, Dihydroxypropyltrimonium Chloride, quaternized hydrolyzed protein such as collagen, oat, wheat, etc . . . , inositol, fructose, sucrose, hydrolyzed plant proteins, seaweed extract, polyethylene glycol, ammonium lactate, sodium hyaluronate, and cyclic peptides.

Some non-limiting examples of occlusive agents which cabn act as skin conditioners include petrolatum, shea butter, avocado oil, balm mint oil, cod liver oil, mineral oil, trimyristin, stearyl stearate, synthetic wax, or mixtures thereof. Some non-limiting examples of other moisturizers include ethyl hexylglycerin, cholesterol, cystine, hyaluronic acid, keratin, lecithin, egg yolk, glycine, PPG-12, polyquaternium polymers such as polyquaternium-11, behentrimonium chloride, dihydroxypropyl PEG-5 linoleammonium chloride, glycerol oleate, PEG-7 glyceryl cocoate, cocoglucoside, PEG-200 hydrogenated glyceryl palmate, panthenol, retinol, salicylic acid, vegetable oil, methyl gluceth-10, methyl gluceth-20, ethoxylated derivatives of skin conditioners such as glycereth-26 and ethoxylated shea butter, and mixtures thereof. Finally, some non-limiting examples of anti-irritants include bisabolol and panthenol.

The skin conditioner or combination thereof in total is present in the composition in an amount from about 0.01 wt. % to about 15 wt. %, preferably from about 0.05 wt. % to about 10 wt. %, and more preferably from about 0.1 wt. % to about 5 wt. %.

Preservatives

The composition may optionally include a preservative. Generally, preservatives fall into specific classes including phenolics, halogen compounds, quaternary ammonium compounds, metal derivatives, amines, alkanolamines, nitro derivatives, biguanides, analides, organosulfur and sulfur-nitrogen compounds, alkyl parabens, and miscellaneous compounds. Some non-limiting examples of phenolic anti-microbial agents include pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof. Some non-limiting examples of halogen compounds include trichlorohydroxy diphenyl ether (Triclosan), sodium trichloroisocyanurate, sodium dichloroisocyanurate, iodine-poly(vinylpyrolidin-onen) complexes, and bromine compounds such as 2-bromo-2-nitropropane-1,3-diol, and derivatives thereof. Some non-limiting examples of quaternary ammonium compounds include benzalkonium chloride, benzethonium chloride, behentrimonium chloride, cetrimonium chloride, and derivatives thereof. Some non-limiting examples of amines and nitro containing compounds include hexahydro-1,3,5-tris(2-hydroxyethyl)-s-triazine, dithiocarbamates such as sodium dimethyldithiocarbamate, and derivatives thereof. Some non-limiting examples of biguanides include polyaminopropyl biguanide and chlorhexidine gluconate. Some non-limiting examples of alkyl parabens include methyl, ethyl, propyl and butyl parabens.

The preservative is preferably present in the composition in an amount from about 0.01 wt. % to about 10 wt. %, preferably from about 0.05 wt. % to about 7.5 wt. %, and more preferably from about 0.1 wt. % to about 5 wt. %.

Thickener

The composition may optionally include a thickener. Exemplary thickeners include (1) cellulosic thickeners and their derivatives, (2) natural gums, (3) starches, (4) stearates, and (5) fatty acid alcohols, (6) acrylic acid polymers and crosspolymers (example "carbomer", (7) Aristoflex AVC (need generic category name0 Some non-limiting examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Some non-limiting examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Some non-limiting examples of starches include oat flour, potato starch, wheat flour, wheat starch, and the like. Some non-limiting examples of stearates include PEG-150 distearate, methoxy PEG-22/dodecyl glycol copolymer, stearic acid flake, and the like. Some non-limiting examples of fatty acid alcohols include caprylic alcohol, cetearyl alcohol, lauryl alcohol, oleyl alcohol, palm kernel alcohol, and the like.

The amount of thickener in the composition depends on the desired viscosity of the composition. The composition preferably has a viscosity low enough to pump through a foamer such as an Airspray foamer and allow foaming. Typical ranges of thickeners include from about 0.001 wt. % to about 2 wt. %, preferably from about %, 0.005 wt. % to about 1 wt. % and more preferably from about 0.01 wt. % to about 0.5%

Carrier

The compositions comprise one or more carriers. Preferred carriers can include, but are not limited to, water and/or water-soluble carriers. Preferred water-soluble carriers include, but are not limited to, alcohols including ethanol, n-propanol, and isopropanol or mixtures thereof. In a preferred embodiment comprising water as a carrier, the water is deionized water or softened water.

The cleansing composition does not require a low pH or a high pH to provide a rapid reduction in microbial populations. Preferably the cleansing compositions have a pH of between about 3.5 and about 9, more preferably between about 4.5 and about 8, and most preferably between about 5.5 and about 7.5 Within this pH range, the compositions effectively reduce microbial populations, and are acceptable for dermal use.

Preferably, the use dilution compositions comprise from about 40 wt. % to about 90 wt. % carrier, more preferably from about 45 wt. % to about 85 wt. % carrier, and most preferably from about 50 wt. % to about 80 wt. % carrier.

Antimicrobial/Sanitizing Agent

Antimicrobials useful in the present compositions include, without limitation, cationic antimicrobial components such as quaternary ammonium compounds and salts thereof, biguanides, substituted biguanides, povidone iodine, and peroxide compounds. Especially preferred are quaternary ammonium compounds having the general structural formula

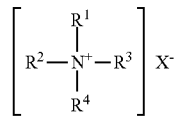

wherein at least one of R.sup.1, R.sup.2, R.sup.3 and R.sup.4 is an alkyl, aryl or an alkylaryl substituent having from 6-26 carbon atoms. Benzalkonium chloride is an especially preferred quaternary ammonium compound for use in the compositions.

The antimicrobial compound may be present up to 5 wt. %, based on the total wt. % of all components in the antimicrobial composition. In some embodiments, the antimicrobial compound is present in amounts ranging from about 0.1 to 3.0 wt. %. In some embodiments, the antimicrobial compound may be present in amounts ranging from about 0.3 to 1.0 wt. %. As used herein unless otherwise specified, the term "wt. %" refers to the amount of actual specified component and not to the wt. % of the commercial version as sold (e.g., where the commercial product is a 50% aqueous solution, the wt. % of the specific component would be half the amount of the commercial product included in the foaming antimicrobial composition). In an embodiment the formulation is triclosan free.

Additional Functional Ingredients

Additional functional ingredients may be used to improve the effectiveness of the composition. Some non-limiting examples of such additional functional ingredients include skin feel improvers, skin conditioners, surfactants pH adjusting compound, preservatives, antioxidants, fragrances, dyes, and the like, as well as mixtures thereof.

EXAMPLES

The foregoing summary, detailed description, and examples provide a sound basis for understanding the invention, and some specific example embodiments of the invention. Since the invention can comprise a variety of embodiments, the above information is not intended to be limiting. The invention resides in the claims.

The reagents used below include:
Alpha-Step® PC-48 is a $C_{10-16}$ sodium methyl 2-sulfolaurate and disodium 2-sulfolaurate available from Stepan;
Stepan-Mild® L3 is a predominantly $C_{12}$ reaction product of lauryl alcohol and lactic acid available from Stepan;
SLES is sodium laureth sulfate;
Cola® Teric is an amphoteric sultaine available from Colonial Chemical, Inc.;
Glucopon® 425N is an alkyl polyglycoside available from BASF Corporation;
Suga® Nate is a sodium laurylglucosides hydrooxypropylsulfonate available from Colonial Chemicals, Inc;
Lathanol® LAL is a sodium lauryl sulfoacetate available from Stepan.

All experiments ran through the SITA Foam Analyzer were as follows:

Equipment:
1) Foaming Apparatus
2) SITA Software

Reagents:
1) 250 mL of each solution
2) DI water

Preparation: Equipment is prepared by turning the water bath on with ample time to warm up before running tests. Adjust water bath to desired temperature.

Quality Assurance: Run a positive and negative control for every experiment. Ensure equipment is clean and free from any residual surfactant chemistry beforehand. In each experiment set, proper differentiation between chemistries can be seen if at least one of the tested chemistries has an "S" curve that depicts a change in the initial foam building and the lathering step.

Experimental Procedure:
1) Prepare water bath
2) Open the "SITA-foam" software on the computer. Project window should be displayed as "Sample 1"

3) Go to "Device" →"Measurement Parameters"
4) Specify desired parameters for the measurement:
   a. Foam Generation
      i. Series Count (cycles): number of measurement replicates (3-triplicate)
      ii. Fill With: Volume of sample liquid (250 mL for each test)
      iii. Stir Count: Number of stirrings for each test (70). This is also the number of measurements for each cycle.
      iv. Stir Time: Stirring duration of sample (10 sec)
      v. Revolution: RPM o the stirrer (900 RMP)
   b. Cleansing
      i. Click the shower icon to activate the automatic cleansing and rinsing function. The vessel will be cleaned automatically after each cycle of measurements.
      ii. Normal cleansing will rinse out the vessel many times. Small cleansing indicates a faster cleansing process. All above parameters can be saved
5) After setting the parameters, click on "Start Measurement" which is the green "Play" button to proceed with the experiment
6) After each cycle of experiments automatic cleansing and rinsing is done in preparation for the next cycle of measurements as long as the instrument is connected to tap water or a cleansing liquid reservoir
7) Each click on the green "Start Measurement" icon opens a new window. The current sample measurement results are all in the same project folder. To rename sample measurement files, right click on the open sample window, and click "save" to rename your sample file
8) If an error occurs at any point with your sample, the measurement reading can be stopped by clicking the red square "Stop icon" or by pressing the large red button on the machine
9) Organize the graph generated with the icons in the fourth section of the tool bar: create new plot, add/remove data from plot, change axis properties, and view properties. Click on the "Create new plot" icon to view the plot after the experiment is done or if it is still running. Right click to rename the plot, insert or remove the plot and display the foam buildup, foam decay, or both Example 1

Establishing initial foaming of the single surfactants is important to establish baselines for comparison for the combinations of various surfactants. To establish the foaming properties of single surfactants, a high amount of each surfactant was analyzed in the SITA Foam Analyzer as described above. The final concentration of each surfactant in solution was 1%. The surfactants tested were sodium lauryl sulfate (SLES), a betaine, Cola® Teric CBS, Glucopon® 425N, Lathanol® LAL, and Suga® Nate 160NC.

As shown in FIG. 1, all of the single surfactants were capable of maxing out the foam reading at around 600 mL of foam. It can also be seen from FIG. 1 that betaine, Cola® Teric CBS and Glucopon® 425N reached saturation at earlier cycles/readings than SLES, Suga® Nate 160NC, or Lathanol® LAL, with SLES taking the longest to reach saturation. This would indicate that betaine, Cola® Teric CBS and Glucopon® 425N have better initial foaming when used as the sole surfactant, while SLES, Suga® Nate 160NC, or Lathanol® LAL all performing more slowly. See raw data for FIG. 1 below Data (contains each separate data point for foam height (mL) that makes up the above graph):

|    | SLES/Alpha Step PC 48 | SLES/Stepan Mild L3 | SLES | DI Water | SLES/ Lanthanol LAL |
|----|----|----|----|----|----|
| 0 | 0 | 0 | 0 | 0 | 0 |
| 1 | 174 | 173 | 147.3 | 10 | 181.25 |
| 2 | 195 | 193 | 161 | 11 | 198.75 |
| 3 | 201.67 | 202 | 168.3 | 8 | 212.25 |
| 4 | 212.3 | 210 | 172.67 | 7 | 228 |
| 5 | 221 | 221.3 | 174 | 8 | 237.75 |
| 6 | 232 | 232 | 177 | 9 | 248.25 |
| 7 | 240.67 | 238.67 | 185.67 | 8 | 259.5 |
| 8 | 248 | 247 | 188.3 | 6 | 273 |
| 9 | 255.67 | 251.67 | 193.67 | 9 | 279.25 |
| 10 | 266 | 257 | 200 | 8 | 283.75 |
| 11 | 273 | 258.67 | 202.3 | 8 | 288 |
| 12 | 276.3 | 260.3 | 204.67 | 8 | 290 |
| 13 | 280 | 263 | 210 | 5 | 292.75 |
| 14 | 283.3 | 265 | 213 | 7 | 294.25 |
| 15 | 284.67 | 264.3 | 217 | 8 | 294.5 |
| 16 | 285.3 | 264.67 | 219.3 | 7 | 295.25 |
| 17 | 286 | 264.3 | 221.3 | 8 | 296 |
| 18 | 286 | 265.3 | 222.67 | 6 | 296.5 |
| 19 | 289.3 | 265.3 | 224.3 | 5 | 297 |
| 20 | 286 | 265.67 | 227.67 | 6 | 297 |
| 21 | 286.3 | 266.3 | 228.3 | 7 | 298 |
| 22 | 286.3 | 267.3 | 231 | 6 | 298.25 |
| 23 | 286.3 | 267 | 232.67 | 5 | 298.5 |
| 24 | 287 | 268.3 | 234.3 | 8 | 299.5 |
| 25 | 288 | 269.3 | 235.3 | 8 | 300.25 |
| 26 | 288 | 270 | 237 | 5 | 301.25 |
| 27 | 288.67 | 272.3 | 237.67 | 6 | 301.5 |
| 28 | 288.67 | 273.3 | 239 | 9 | 303.5 |
| 29 | 289 | 275.67 | 239.67 | 3 | 305.75 |
| 30 | 290.67 | 278 | 240 | 5 | 307.5 |
| 31 | 291.3 | 281.3 | 240.67 | 4 | 310 |
| 32 | 292.3 | 284 | 241.3 | 5 | 313 |
| 33 | 293 | 286.67 | 242.3 | 6 | 315.25 |
| 34 | 295 | 290 | 243 | 6 | 318.5 |
| 35 | 297 | 293.67 | 243 | 3 | 321.25 |
| 36 | 299 | 298 | 243.67 | 7 | 325 |
| 37 | 300 | 300.67 | 244 | 5 | 327.75 |
| 38 | 302.67 | 305 | 245.3 | 6 | 332.75 |
| 39 | 305.67 | 309.3 | 245 | 5 | 336 |
| 40 | 307.3 | 313.3 | 245 | 6 | 339.75 |
| 41 | 311.67 | 317.67 | 245.67 | 5 | 343 |
| 42 | 314.3 | 321.67 | 246 | 8 | 347 |
| 43 | 317 | 325.67 | 246 | 6 | 352.25 |
| 44 | 320.3 | 329 | 246.67 | 4 | 356.5 |
| 45 | 323.67 | 334 | 246.67 | 4 | 360.25 |
| 46 | 326.3 | 337.3 | 246.67 | 8 | 366 |
| 47 | 331 | 342 | 247 | 5 | 369.75 |
| 48 | 334.3 | 346.3 | 247.67 | 5 | 377.75 |
| 49 | 337.3 | 351 | 247.67 | 9 | 386 |
| 50 | 341 | 354.3 | 248 | 5 | 412.75 |
| 51 | 343.67 | 360 | 248.67 | 6 | 438 |
| 52 | 349 | 364.3 | 248.67 | 3 | 446.25 |
| 53 | 352 | 369.3 | 248.67 | 6 | 452 |
| 54 | 357.3 | 373.67 | 250 | 5 | 462.75 |
| 55 | 359.67 | 377.67 | 250.3 | 6 | 493.25 |
| 56 | 368.67 | 386 | 251.3 | 5 | 520.25 |
| 57 | 372.3 | 392 | 250.3 | 4 | 543.75 |
| 58 | 377.3 | 396 | 250 | 5 | 598 |
| 59 | 384 | 404.67 | 251 | 5 | 627.5 |
| 60 | 391 | 419.3 | 251.3 | 6 | 636.75 |
| 61 | 397.3 | 484.67 | 251.67 | 8 | 641 |
| 62 | 422.3 | 582.3 | 252.67 | 5 | 644.75 |
| 63 | 465.3 | 622.67 | 252 | 3 | 646.75 |
| 64 | 476.3 | 635.67 | 253 | 5 | 646.75 |

-continued

| SLES/Alpha Step PC 48 | SLES/Stepan Mild L3 | SLES | DI Water | SLES/ Lanthanol LAL |
|---|---|---|---|---|
| 65 | 504 | 642.67 | 253.67 | 4 | 646.75 |
| 66 | 545.3 | 650 | 253.67 | 6 | 647.5 |
| 67 | 571.3 | 655 | 253.67 | 5 | 647.5 |
| 68 | 614 | 656.3 | 253 | 4 | 647.75 |
| 69 | 626.3 | 658.3 | 253 | 1 | 648.25 |
| 70 | 632.3 | 659 | 254 | 5 | 647.5 |

Figure 2:
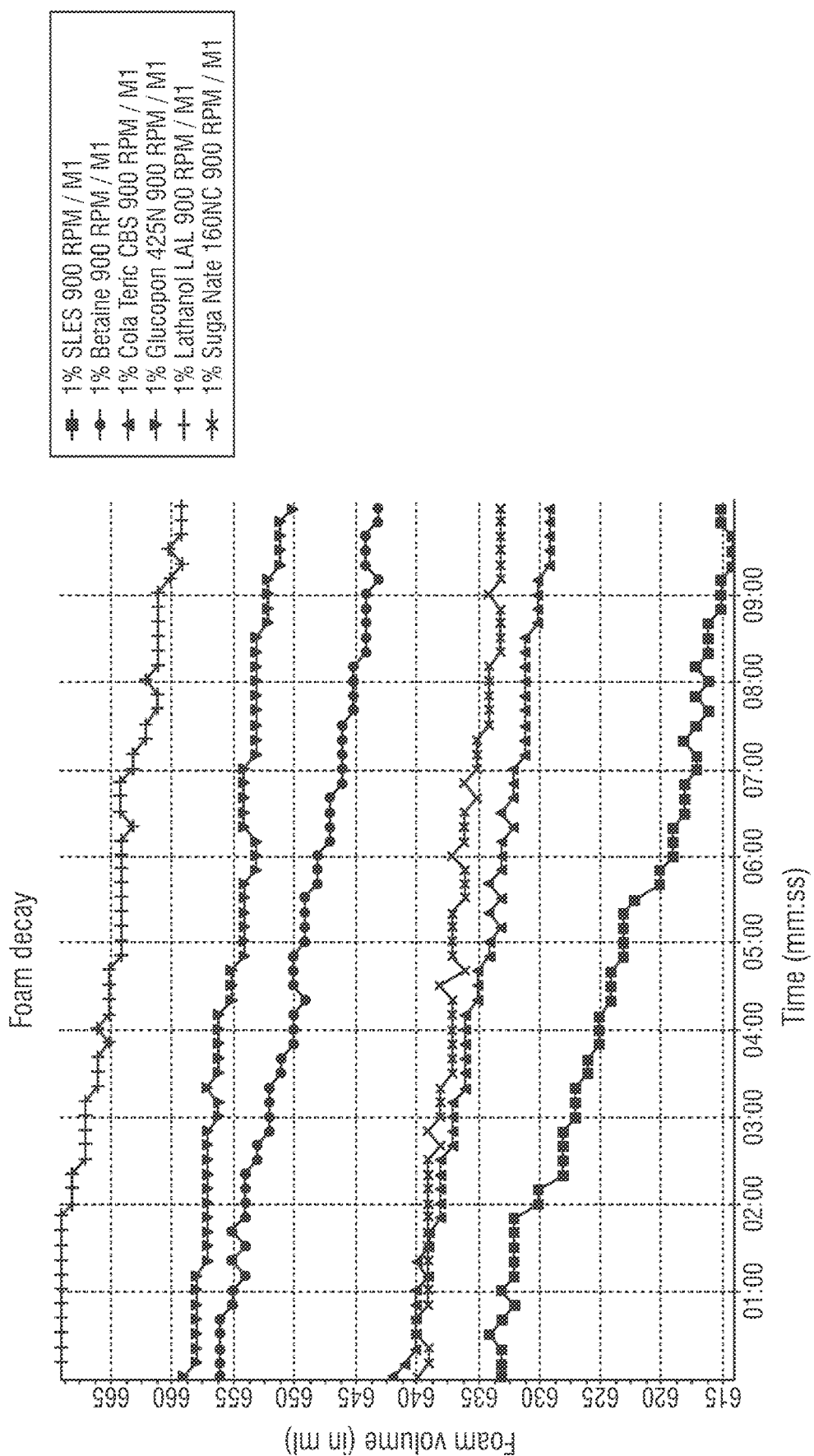
FIG. 2 is a graphical representation of the foam decay of 1 wt. % solutions of SLES, betaine, Cola® Teric CBS, Glucopon® 425N, Lathanol® LAL, and Suga® Nate 160NC.

The foam decay time was also measured. As shown in FIG. 2, all the surfactants showed a loss in foaming over time. SLES had the largest drop in foaming with a loss of about 20 mL of foaming over 10 minutes. The other tested surfactants also dropped in foaming amount, but only between about 5 to about 10 mL in volume over 10 minutes.

Taken together, these results show that SLES has the slowest onset to foaming and loses foaming the quickest. The results also show that betaine, Cola® Teric CBS and Glucopon® 425N came to maximum foaming levels the quickest and had similar foam decay. These results would indicate that mixtures of surfactants similar to betaine, Cola® Teric CBS and Glucopon® 425N would have more desirable foaming properties than mixtures of surfactants similar to Lanthanol® LAL, Suga® Nate 160NC, or Cola® Teric CBS.

Example 2

As it is unknown, generally, if any one surfactant will have an influence on the foaming or performance of another surfactant and if so, if that influence will increase or decrease the characteristics of the other surfactant, several surfactants were tested in mixes with sodium laureth sulfate (SLES).

Alpha-Step® PC-48, Stepan-Mild® L3, and Lanthanol® LAL were individually combined with SLES in a use solution and had a final concentration of 50 ppm (0.005 wt. %) with SLES having a final concentration of 2,000 ppm (0.2 wt. %), with SLES alone as a positive control and DI water used as a negative control. The compositions were tested for foaming using the SITA Foam Analyzer as described above. The lower amount of SLES used was to prevent it from saturating the SITA Analyzer.

Figure 3:
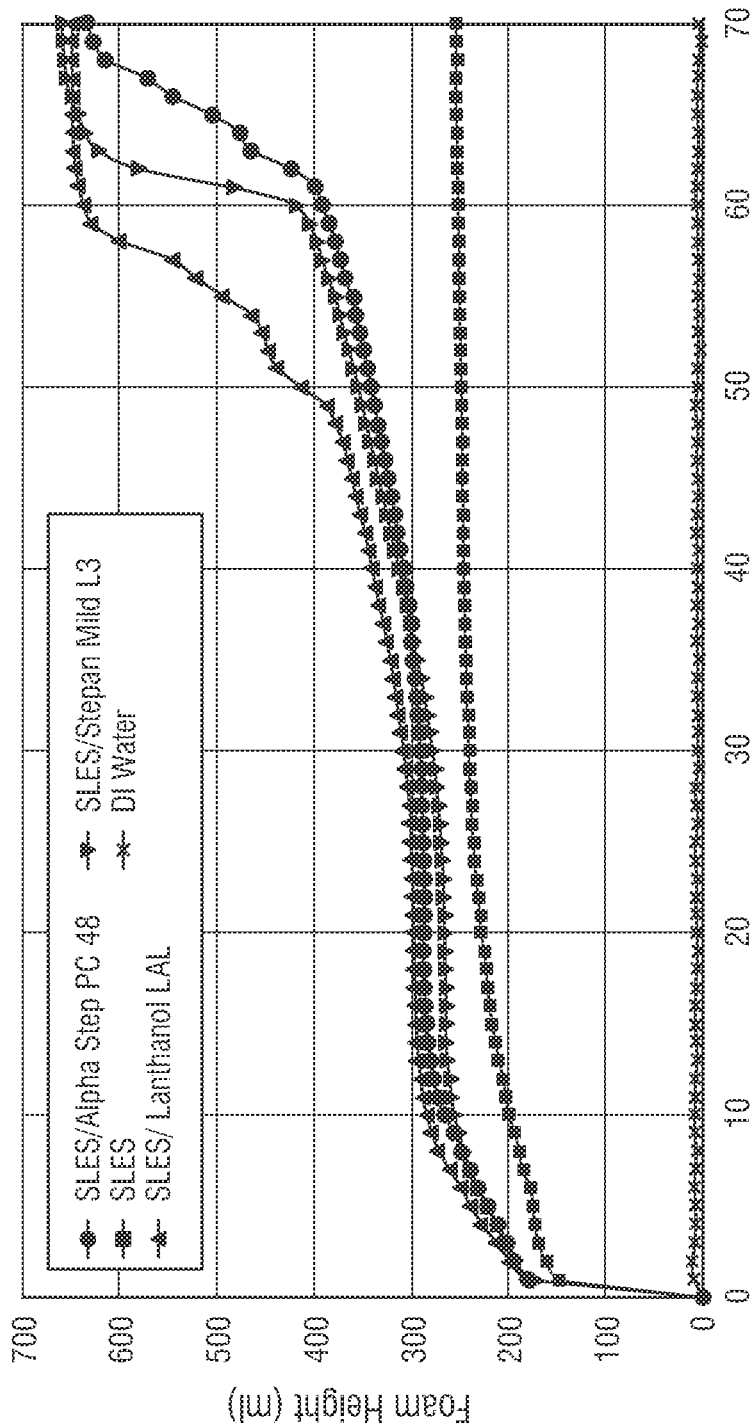
FIG. 3 is a graphical representation of foam formation for combinations of 0.2 wt. % SLES with 0.005 wt. % Alpha® Step PC48, Stepan Mild L3, Lathanol® LAL.

As shown in FIG. 3, SLES at the lower concentration than what was used in Example 1 was unable to reach saturation, each of the combinations were capable of reaching saturation of foam and for about the first 49 cycles (490 seconds) had similar amounts of foam, the combination of SLES with Lanthanol® LAL had a quicker foaming response compared to the other two mixtures.

These results indicate that SLES, at lower concentration, can be made to foam by the addition of a low amount of a secondary surfactant. Further, it appears, unlike in Example 1, that when combined with Lanthanol® LAL, surprisingly the combination had superior performance to other combinations of surfactants with SLES.

Example 3

The foam creation and decay of surfactant combinations was also tested in the SITA Analyzer. SLES was combined with betaine, Cola® Teric CBS, Lanthanol® LAL, Glucopon® 425N, or Suga® Nate 160N. The total amount of surfactant used was 1 wt. % of the solution, similar to that in Example 1.

Figure 4:
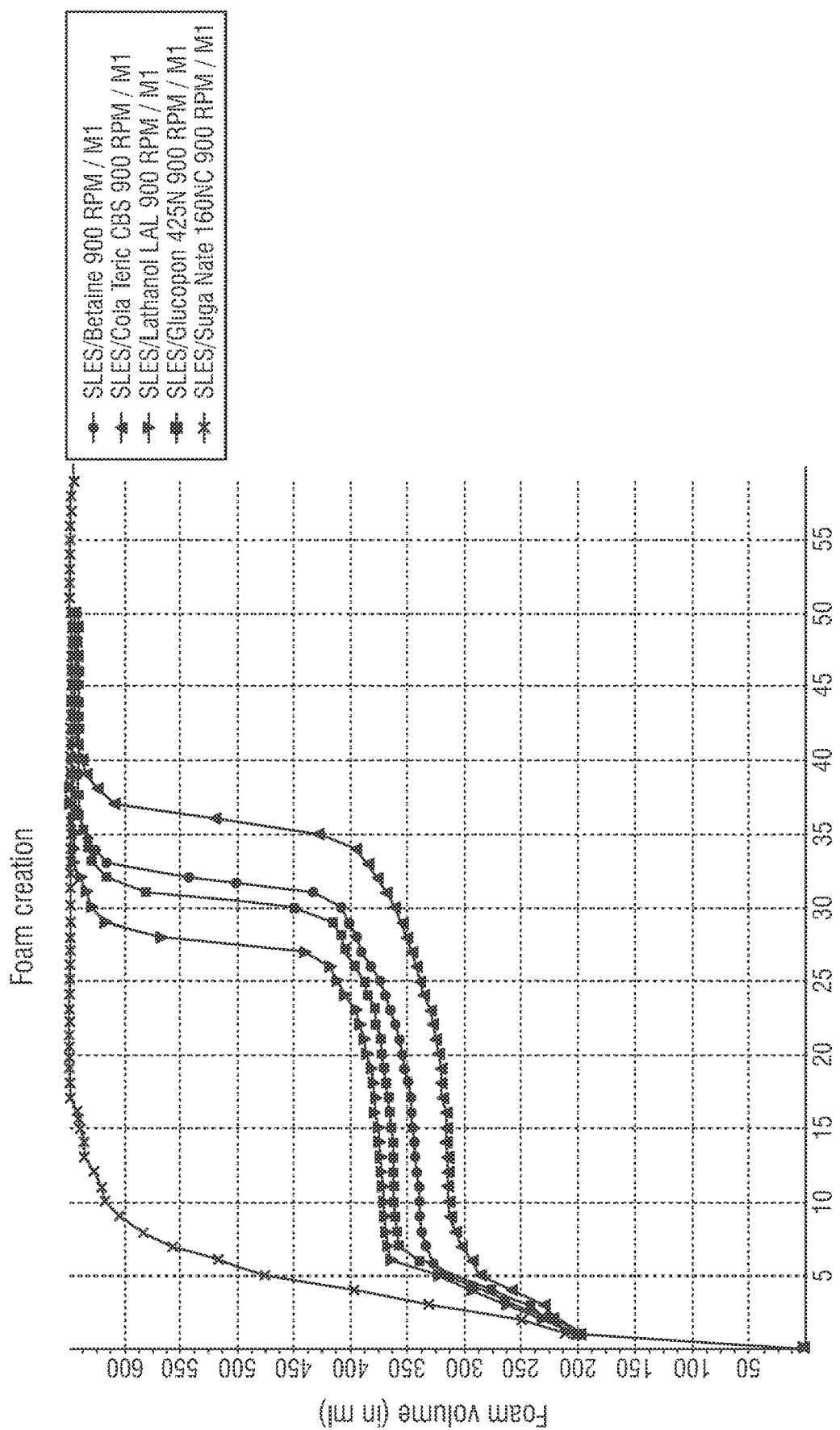
FIG. 4 is a graphical representation of foam formation of SLES with betaine, Cola® Teric CBS, Lathanol® LAL, Glucopon® 425N, or Suga® Nate 160NC, with a final concentration of 1 wt. % of surfactants.

As shown in FIG. 4, unlike in Example 1, SLES combined with either Suga® Nate 160NC or Lanthanol® LAL had faster foam creation than when SLES was combined with Cola® Teric CBS, Glucopon® 425N, or betaine. This is surprising given the superior foam creation properties of these three surfactants when compared to the initial results of Suga® Nate 160NC or Lanthanol® LAL. These surprising results suggest that SLES works in synergy with these two surfactants to improve initial foaming properties.

Figure 5:
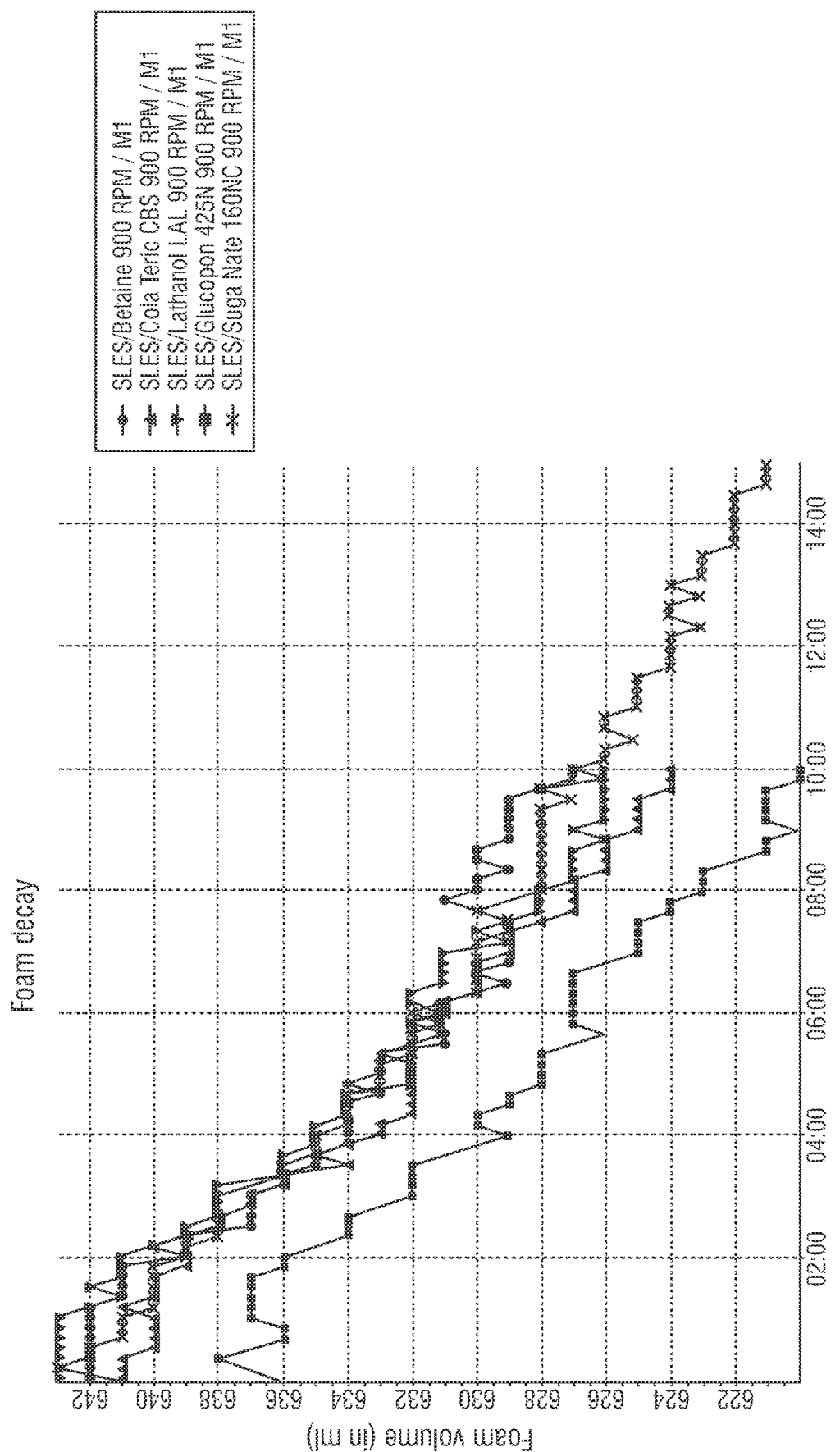
FIG. 5 is a graphical representation of foam decay of SLES with betaine, Cola® Teric CBS, Lathanol® LAL, Glucopon® 425N, or Suga® Nate 160NC, with a final concentration of 1 wt. % of surfactants

Similarly, the foam decay patterns were different when SLES was combined with one of the above surfactants. Comparing the results in FIG. 2 with FIG. 5, the addition of a second surfactant lowered the amount of foam lost when SLES was used alone. Alone, SLES lost about 20 mL of foam in 10 minutes (FIG. 2) compared to losing about 15 mL when combined with a second surfactant within the same 10-minute period.

Taken together, the addition of a secondary surfactant improves both the creation and decay of foam than when SLES is used alone. Surprisingly, Suga® Nate 160NC and Lathanol® LAL showed the best improvements in foam formation when combine with SLES given the seemingly better foam formation of the other surfactants when used alone.

Example 4

Additional combinations of the surfactants with other ingredients were also tested to compare the foaming properties when combined with formulation containing Lanthanol® LAL to those without.

TABLE 3

Test solutions, amounts indicate wt. %.

| Compound | 113 | 159 | 160 | 161 | 162 |
|---|---|---|---|---|---|
| Purified Water | 74.70 | 71.95 | 69.55 | 69.10 | 70.69 |
| SLES, 60% | 9.80 | 9.30 | 9.30 | 9.30 | 9.30 |
| Amphoteric/nonionic surfactants | 8.70 | 9.10 | 9.10 | 9.10 | 9.10 |
| Lanthanol LAL, 65% | 2.00 | 1.50 | | | |
| Stepan mild LSB, 25% | | | 5.20 | | |
| Stepan mild PCL, 23% | | | | 5.65 | |
| Stepan mild SL3-BA, 32% | | | | | 4.06 |
| Additional functional components: humectants, skin conditioners, emollients, preservatives, thickeners | 4.8 | 7.7 | 6.85 | 6.85 | 6.85 |
| Total | 100.00 | 103.00 | 100.50 | 99.50 | 94.00 |
| Total Active Surfactant | 10.71 | 10.71 | 9.94 | 9.995 | 6.575 |

When comparing the composition containing Lanthnaol® LAL to those without, those with Lanthanol® LAL created a very dense lather that completely covered the area and builds well. The other foaming surfactant had good initial foaming but decreased in the presence of lotion or mild soil. Therefore, in the presence of additional compounds, such as glycerine.

Example 5

As the addition of Lanthanol® LAL changes the foaming properties of the compositions, its influence on preservatives was also tested.

TABLE 4

Compositions for preservative testing, amounts in wt. %.

| Compound | 11 | 12 | 13 | 14 | 15 | 16 | 17 |
|---|---|---|---|---|---|---|---|
| Water | 78 | 77 | 76.5 | 76 | 77 | 77 | 76.5 |
| SLES, 60% | 9.016 | 9.016 | 9.016 | 9.016 | 9.016 | 9.016 | 9.016 |
| Amphoteric/nonionic surfactants | 7.176 | 7.176 | 7.176 | 7.996 | 7.176 | 7.176 | 7.176 |
| Lathanol LAL powder, 65% | 1.84 | 1.84 | 1.84 | 1.84 | 1.84 | 1.84 | 1.84 |
| Additional functional components: humectants, skin conditioners, emollients, preservatives, thickeners | 4.653 | 4.97 | 5.47 | 5.14 | 4.97 | 4.97 | 5.47 |
| Total | 100 | 100 | 100 | 100 | 100 | 100 | 100 |
| Total Active Surfactant | 9.46 | 9.46 | 9.46 | 9.45 | 9.46 | 9.46 | 9.46 |

The 7 different compositions in Table 4 were tested for their preservative ability, with composition 11 being a negative control as it lacks either phenoxyethanol or benzoic acid. To test the compositions, a bacterial inoculum and a yeast and mold inoculum were created. The bacterial inoculum comprised of equal parts of *Staphylococcus aureus* (ATCC 6538), *Escherichia coli* (ATCC 11229), *Enterobacter aerogenes* (ATCC 13048), *Burkholderia cepacian* (ATCC 25416), and *Pseudomonas aeruginosa* (ATCC 15442). The yeast and mold inoculum comprised of equal parts of *Candida albicans* (ATCC 10231), *Saccharomyces cerevisiae* (ATCC 834), and *Aspergillus niger* (ATCC 16404).

The inoculates were incubated for 3 days with the bacterial inoculum at 32° C. and the yeast and mold inoculum at 26° C. The preservative compositions were added, and samples measured at 7, 14, 21, and 28 days. A sample passed if no bacteria or yeast and mod survived after Day 7, conditionally passed if there was a greater than 2.0 log reduction on day 7 when compared to day 3, with no additional growth on days 14, 21, or 28 for the bacterial samples, and if there was not more than a 0.5 log increase from the initial inoculated count at days 14 and 28 for the yeast and mold samples. The results are summarized in Table 5 for bacterial samples and Table 6 for yeast and mold.

TABLE 5

Results of bacterial samples.

| Sample Number | Day 0 | Day 7 | Day 14 | Day 21 | Day 28 | Pass/Fail |
|---|---|---|---|---|---|---|
| 11 | <0.1 | 6.96 | 6.95 | 6.93 | 6.96 | Fail |
| 12 | <0.1 | 4.40 | 2.54 | <1.0 | <1.0 | Conditional Pass |
| 13 | <0.1 | 4.18 | 2.15 | <1.0 | <1.0 | Conditional Pass |
| 14 | <0.1 | 4.43 | 3.63 | 2.20 | <1.0 | Conditional Pass |
| 15 | <0.1 | 4.30 | 2.64 | <1.0 | <1.0 | Conditional Pass |
| 16 | <0.1 | 4.68 | 3.08 | 1.85 | <1.0 | Conditional Pass |
| 17 | <0.1 | 4.67 | 2.54 | 1.00 | <1.0 | Conditional Pass |

TABLE 6

Results for yeast and mold inoculum.

| Sample Number | Day 0 | Day 7 | Day 14 | Day 21 | Day 28 | Pass/Fail |
|---|---|---|---|---|---|---|
| 11 | <1.0 | 5.64 | 5.80 | 5.66 | 5.81 | Conditional Pass |
| 12 | <1.0 | 5.57 | 5.49 | 5.40 | 5.59 | Conditional Pass |
| 13 | <1.0 | 2.89 | <1.0 | <1.0 | <1.0 | Pass |
| 14 | <1.0 | 3.05 | 1.60 | <1.0 | <1.0 | Conditional Pass |
| 15 | <1.0 | 2.90 | <1.0 | <1.0 | <1.0 | Pass |
| 16 | <1.0 | 3.08 | 1.70 | 1.00 | 1.00 | Conditional Pass |
| 17 | <1.0 | 2.72 | <1.0 | <1.0 | <1.0 | Pass |

As can be seen from the results of Tables 5, by day 28 all the compositions reduced the bacterial count to <1.0 indicating that the inclusion of Lathanol® LAL does not interfere with the addition of preservatives into the compositions. The results also indicate that Lathanol® LAL does not interfere with the antifungal or antimold capabilities either. While phenoxyethanol is known to have antifungal properties, it is typically combined with other antifungals when used in less than a 2 wt. % in a composition. Therefore, it is not surprising that sample 12 did not perform as well as the other samples, having similar results to sample 11, the negative control.

Therefore, Lathanol® LAL may be included in various preservative composition without interfering with their antifungal or antibacterial properties.

What is claimed is:

1. A liquid cleansing composition comprising:
    from about 0.1% to about 40% by weight of an anionic sulfate surfactant and/or a sulfonated alcohol, including salt forms thereof, wherein said anionic sulfate surfactant comprises sodium laurylglucosides hydroxypropylsulfonate and sodium laureth sulfate;
    from about 0.01 to about 10 wt. % of an alkyl sulfoacetate surfactant and/or salt forms thereof, wherein said alkyl sulfoacetate is an ethoxylated alkyl sulfoacetate;
    from about 0.1% to about 15% by weight of nonionic, cationic or zwitteronic surfactant, and
    from about 0.1% to about 50% by weight of additives, with the balance being a carrier up to 100%, wherein said composition is free of sulfonated fatty acids.

2. The cleansing composition of claim 1, further comprising one or more additional sulfate surfactants.

3. The composition of claim 1, wherein the sulfate surfactant further comprises a linear alkyl sulfate.

4. The composition of claim 1 further comprising a preservative.

5. The composition of claim 1, wherein the additives are selected from the group consisting of emollients, thickeners, humectants, salts, skin conditioning agents, fragrances, colors, herbal extracts, builders, pH adjusters, antibacterial agents, vitamins, antioxidants, pearlescent agents, opacifiers, and preservatives.

6. The composition of claim 1, further comprising an additional nonionic, cationic, or zwitteronic surfactant.

7. The composition of claim 1, further comprising a betaine, sultaines, amine oxides, hydroxysultaines, sulfosuccinates, amphoacetates, sarcosinates, and/or acyl lactylate surfactant.

8. The composition of claim 1, wherein the composition is diluted to form a use solution.

9. A method of cleansing a dermal surface comprising:
 applying the cleansing composition of claim 1 and thereafter,
 rising said composition from said dermal surface, so that debris and other contaminants are removed.

10. The method of claim 9 wherein said dermal surface includes hair or scalp.

11. The method of claim 9 wherein said dermal surface is skin.

12. A non-aerosol foaming composition suitable for use as a skin cleanser or shampoo comprising:
 from about 0.1% to about 40% by weight of an anionic sulfate surfactant and/or a sulfonated alcohol, including salt forms thereof, wherein said anionic sulfate surfactant comprises sodium laurylglucosides hydroxypropylsulfonate and sodium laureth sulfate;
 from about 0.01 to about 10 wt. % of an alkyl sulfoacetate surfactant and/or salt forms thereof, wherein said alkyl sulfoacetate is an ethoxylated alkyl sulfoacetate;
 from about 0.1% to about 15% by weight of nonionic, cationic or zwitteronic surfactant,
 from about 0.01 to about 15% by weight of a skin conditioner,
 from about 0.1% to about 50% by weight of additives, with the balance being a carrier up to 100%.

13. The composition of claim 12, wherein the additives are selected from the group consisting of emollients, emulsifiers, rheological modifiers, humectants, salts, skin conditioning agents, fragrances, colors, herbal extracts, vitamins, builders, enzymes, pH adjusters, antibacterial agents, preservatives, opacifiers, pearlescent agents, and mixtures thereof.

14. The composition of claim 12, further comprising one or more additional sulfate surfactants.

15. The composition of claim 12 further comprising a preservative.

16. The composition of claim 12, further comprising an additional nonionic, cationic, or zwitteronic surfactant.

17. The composition of claim 12, further comprising a betaine, sultaines, amine oxides, hydroxysultaines, sulfosuccinates, amphoacetates, sarcosinates, and/or acyl lactylate surfactant.

\* \* \* \* \*